United States Patent [19]

Manos

[11] Patent Number: 5,084,345

[45] Date of Patent: Jan. 28, 1992

[54] LAMINATES UTILIZING CHEMICALLY ETCHABLE ADHESIVES

[75] Inventor: Philip Manos, Wilmington, Del.

[73] Assignee: E. I. Du Pont de Nemours and Company, Wilmington, Del.

[21] Appl. No.: 618,112

[22] Filed: Nov. 26, 1990

[51] Int. Cl.⁵ .......................... B32B 27/38; C09J 3/14
[52] U.S. Cl. .................... 428/335; 428/413;
428/910; 428/414; 428/416; 428/458;
156/331.1; 156/307.7; 174/254; 361/397;
361/398; 523/400; 528/289
[58] Field of Search ............ 428/413, 414, 473.3,
428/335, 446, 910, 458

[56] References Cited

U.S. PATENT DOCUMENTS

| | | | |
|---|---|---|---|
| 3,728,150 | 4/1973 | Yuan | 117/138.8 |
| 3,822,175 | 7/1974 | Yuan | 161/93 |
| 3,900,662 | 8/1975 | Yuan | 428/252 |
| 4,064,192 | 12/1977 | Bargain | 260/857 |
| 4,517,321 | 5/1985 | Gardner et al. | 523/400 |
| 4,528,373 | 7/1985 | D'Alelio et al. | 546/66 |
| 4,579,885 | 4/1986 | Domeier et al. | 523/400 |
| 4,711,964 | 12/1987 | Tan et al. | 548/461 |
| 4,801,682 | 1/1989 | Scola | 528/353 |
| 4,814,357 | 3/1989 | Indyke | 528/289 |
| 4,816,493 | 3/1989 | Indyke | 521/110 |
| 4,842,949 | 6/1989 | Gagliani et al. | 428/473.3 |
| 4,851,495 | 7/1989 | Sheppard et al. | 528/170 |
| 4,859,530 | 8/1989 | Roark et al. | 428/473.5 |
| 4,898,971 | 2/1990 | Slack | 560/359 |
| 4,937,133 | 6/1990 | Watamabe | 428/473.3 |

FOREIGN PATENT DOCUMENTS 2101526  4/1982  United Kingdom .

*Primary Examiner*—P. C. Sluby

[57] ABSTRACT

A multilayer laminate having a metallic layer and a dielectric layer, such as a chemically etchable polyimide, bonded to each other with a chemically etchable adhesive containing phenolic ester groups in the backbone.

5 Claims, No Drawings

LAMINATES UTILIZING CHEMICALLY ETCHABLE ADHESIVES

FIELD OF THE INVENTION

This invention relates to laminates utilizing chemically etchable adhesives containing phenolic ester groups in the backbone, for bonding at least one layer or film to another layer, such as a flexible metallic layer on a flexible layer of a dielectric material such as a chemically etchable polyimide, in order to form an etchable multilayer metal-clad laminate.

BACKGROUND OF THE INVENTION

Laminates comprising one or more layers of dielectric material, such as polyimide and one or more layers of metallic substrate material may be used for a variety of applications. For example, polyimide coated metal foils, due to the flexibility and outstanding mechanical, thermal and electrical properties of polyimides, can be used for printed electrical circuits. This is because the laminates are frequently exposed to high temperatures during further processing, for example, during soldering or drilling. The laminates also have to satisfy stringent requirements in regard to their electrical and mechanical properties.

Laminates comprising only one substrate layer of metal or metal alloy and a layer of polyimide, so called single clads, may be used for printed electrical circuits. The same applies to multilayer laminates, so called multi-clads or multilayer circuits, which comprise several metal layers and/or several polyimide layers.

The metal layers are usually etched by methods well known in the art to form conductive paths on the polyimide layer.

Especially in the case of multi-clads, it is necessary to form small vias or other holes of various sizes through the polyimide and adhesive layers, or through the whole clad. This is necessary in order to electrically connect the conductive metal paths disposed within different layers, or for other purposes such as, for example, forming conductive bridges, inserting electronic components, and the like. Flexible circuits and tape automated bonding parts are examples where laminates using adhesives and techniques of the present invention are very useful.

Although in a number of occasions, the vias or holes may be punched, mechanically drilled, or laser drilled, it is desirable in many other occasions to use chemical etching techniques for this purpose. In the case where the method of opening the vias or holes is chemical etching, it is obviously necessary to use etchable materials as a dielectric film and as an adhesive.

Laminates containing polyimides and metal substrates are well-known in the art. Usually the polyimide layers are bonded to the metal substrate by a conventional adhesive. For example, U.S. Pat. No. 3,900,662, U.S. Pat. No. 3,822,175, and U.S. Pat. No. 3,728,150 disclose bonding of polyimide to metal using an acrylate-based adhesive. However, it has been found that when conventional adhesives, such as acrylates for example, are used to bond the polyimide to the metal, the resulting laminates do not exhibit entirely satisfactory properties which meet the stringent demands often imposed. In addition, they do not possess chemical etching characteristics.

Thus, adhesives initially based on epoxy chemistry and later based on imide chemistry became of higher preference, but still the problem of inability to etch these adhesives remained mostly unresolved. In order to avoid the use of adhesives at all, multilayer laminates have been proposed in which the polyimide is bonded directly to metal, i.e., without a layer of adhesive. Thus, British Patent 2,101,526 discloses the bonding of a polyimide derived from biphenyltetracarboxylic dianhydride directly to metal foil by applying heat and pressure. The whole polyimide layer of this laminate, however, is subject to inferior thermal stability as compared to laminates made from layers of conventional polyimides. Further, the selection of polyimides to be used in such laminates is limited.

Currently available acrylic and epoxy based adhesives are non-etchable chemically, while long molecular weight linear polyimides may be often chemically etchable. However, the linear polyimides, in order to have adequate physical properties they must be of high molecular weight, which in turn brings about a serious disadvantage. The solution viscosity of these polyimides is excessively high at reasonable solids content levels. This renders them impractical as adhesives, since a very large number of layers have to be applied before reaching a reasonable thickness.

Thus, according to this invention, cross-linkable or extendable oligomers are preferred, which contain in their backbone phenolic ester bonds, defined as bonds which are the reaction product of a carboxylic acid with a phenolic hydroxyl group. The oligomers may be easily selected to have low viscosity, due to their low molecular weight. The molecular weight is then increased in the laminate by cross-linking or extension as described in more detail later, and the chemical etchability is brought about by the incorporated phenolic ester groups.

U.S. Pat. No. 4,517,321 (H. C. Gardner, et al.) discloses resins with improved tensile properties and compressive strength by using as curing agents such diamines as aromatic dietherdiamines, among which a diester diamine made from bisphenol A by esterification with meta-aminobenzoic acid is also disclosed. However, no mention or suggestion is made regarding the difference, which is of utmost importance to the present invention, of this particular diester diamine when compared to the plethora of the rest of the diether diamines. This difference, which is immaterial for the purposes of the invention disclosed in U.S. Pat. No. 4,517,321, is the fact that a diester diamine resulting from a carboxylic acid, such as, for example, aminobenzoic acid and a phenolic hydroxyl bearing compound, such as bisphenol A, provides chemical etchability to the cured product. The same comments apply to U.S. Pat. No. 4,579,885 (Linda A. Domeier, et al.), which also discloses similar compositions.

U.S. Pat. No. 4,898,971 (W. E. Slack) discloses liquid isocyanate prepolymers made from aromatic diisocyanates and lengthy, flexible diamines some of which may use ester functions to link flexible segments. However, again nothing is mentioned, suggested or implied regarding the etchability-imparting difference between the aforementioned special ester group and the rest of the compositions.

U.S. Pat. No. 4,851,495 (Sheppard et al.) discloses polyetherimide oligomers having cross-linking and end cap moieties, which provide improved solvent-resistance to cured composites. It also discloses blends generally comprising substantially equimolar amounts of the oligomers and a comparable, compatible, non-crosslinking, etherimide polymer of substantially the same backbone. Sheppard utilizes all aromatic moieties with ether (—O—) or thioether (—S—) linkages as flexibilizing functions. To achieve any melt flow away from cure temperatures, m in his formula must be kept no more than 0 or 1. However, this makes the cured resin brittle and suitable only for rigid laminates and/or composites. Even for those applications, brittleness is probably the reason for resorting to blends with reactive plasticizers.

U.S. Pat. No. 4,801,682 (Scola) discloses high temperature polyimides, which are typically the copolymerization product of about 3 mole % to about 42 mole % nadic esters; about 39 mole % to about 49 mole % diamine; and about 17 mole % to about 48 mole % 4,4', 9 (2,2,2-trifluoro-1-phenyletheridene)-biphthalic tetracarboxylic acid dialkylester. This chemistry deals with structural composites, where evolution of volatiles is not important. There is an abundance of volatiles because this chemistry involves partial esters of di- and tetracarboxylic acids with lower alcohols, which must be liberated during cure.

U.S. Pat. No. 4,711,964 (Tan et al.) discloses bisbenzocyclobutene aromatic imide oligomers. This chemistry also involves structural composites, not suitable for adhesives. Benzocyclobutene end groups may be cured by Diels-Alder conditions requiring high temperatures, and lengthy times, as well as presence of dienenophiles such as commercial bismaleimides, generally leading to brittle resins.

U.S. Pat. No. 4,528,373 (D'Alelio et al.) discloses unsaturated vinylacetylene-terminated polyimides and processes for their preparation. This invention involves high molecular weight polymers terminated in acetylenic functions requiring high post cure temperatures. The cure temperatures may be lowered by mixing in free radical initiators, which however, are inevitably incorporated in the resin with unknown impact on properties.

U.S. Pat. No. 4,064,192 (Bargain) discloses heat-stable resins having good mechanical and electrical properties combined with chemical inertness at temperatures of 200 to 300° C., which resins are resins of a three-dimensional polyimide which is obtained by reacting, at between 50° C. and 350° C., a bisimide of the general formula:

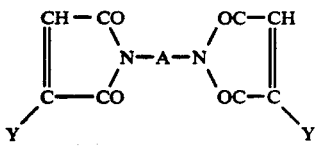

in which Y denotes H, $CH_3$ or Cl, and A represents a divalent organic radical possessing at least two carbon atoms, a polyamine of the general formula:

in which x represents an integer at least equal to 2 and R denotes an organic radical of valency x, and an alazine of the general formula:

in which G represents a monovalent aromatic radical, and a polymerizable monomer other than a bisimide, containing at least one polymerizable vinyl, maleic, allyl or acrylic —CH=C< group in amounts such that if $N_1$ represents the number of moles of bisimide employed, $N_2$ represents the number of moles of polyamine employed, and $N_3$ represents the number of moles of alazine employed, the ratio $$\frac{N_1}{\frac{2N_2}{x} + N_3}$$

is at least 1.3, x being defined as above.

U.S. Pat. Nos. 4,814,357 and 4,816,493 (Indyke) disclose described flexible polyimide foams having enhanced compression fatigue life and softness for use in the manufacture of seat cushions and methods for the production of such foams and precursors therefor. These foams are produced from novel polyimides prepared by reaction of an organic tetracarboxylic acid or derivative thereof, preferably an ester with (a) about 1 to about 50 mole percent of a diester of (i) a primary amino-substituted aromatic carboxylic acid, and (ii) a polymethylene glycol, and (b) at least one aromatic or heterocyclic primary diamine. Foams can be produced having (a) a fatigue life as determined by ASTM test procedure D3574-81 using foam specimens from three to five inches in thickness of at least 15,000 cycles, or (b) an indentation force deflection as determined by ASTM test procedure D3574-81 on foam specimens of one-inch thickness of less than 40 pounds of force at 25% deflection and less than 180 pounds of force at 65% deflection, or both of (a) and (b).

SUMMARY OF THE INVENTION

According to this invention, there are provided laminates of at least one layer or film bonded by a chemically etchable adhesive to another layer or film, preferably a flexible metallic layer bonded to a layer of an also chemically etchable flexible polyimide, in which vias and other openings may be formed by chemical etching, and preferably alkaline chemical etching. More particularly, this invention pertains to a laminate having a substrate coated with a cross-linkable composition comprising a reactive oligomer having in the backbone hydrolyzable phenolic ester groups of an equivalent weight in a range from 200 to 10,000, with the requirement that a 50 micrometer thick film of the composition after cure disintegrates within 50 cycles of alternatingly submersing the film in a stirred solution containing by weight 13% potassium hydroxide, 11% distilled water, and 76% ethanol at 60° C. for 1 minute, and in a stirred bath of deionized water at 60° C. for 30 seconds, wherein one submersion in the ethanolic potassium hydroxide solution followed by one submersion in the deionized water constitutes one cycle.

Preferably, the substrate may be metallic, such as copper, or it may be polymeric, such as an etchable polyimide. Also preferably, the etchable adhesive may comprise an epoxy, or even more preferably an oligoimide.

Also, this invention pertains to a laminate comprising a metallic layer, an etchable polyimide layer, and an adhesive composition layer therebetween, the adhesive composition comprising a cross-linked reactive oligomer having in the backbone hydrolyzable phenolic ester groups of an equivalent weight in a range from 299 to 10,000, with the requirement that a 50 micrometer thick film of the composition after cure disintegrates within 50 cycles of alternatingly submersing the film in a stirred solution containing by weight 13% potassium hydroxide, 11% distilled water, and 76% ethanol at 60° C. for 1 minute, and in a stirred bath of deionized water at 60° C. for 30 seconds wherein one submersion in the ethanolic potassium hydroxide solution followed by one submersion in the deionized water, constitutes one cycle.

The preferred metallic layer is copper and the preferred cross-linked reactive oligomer comprises a cross-linked epoxy, and even more preferably a cross-linked oligoimide.

DETAILED DESCRIPTION OF THE INVENTION

The adhesives employed in making the laminates of the present invention may also be utilized in general as adhesives for miscellaneous other substrates. They are, however, especially suited, as adhesives for etchable polyimide layers or films to be bonded to metal layers or films, preferably copper, in order to form flexible polyimide metal-clad laminates having a peel strength of at least 3 pli (I.P.C. Standard Method 2.4.9, "Peel Strength, Flexible Printed Wiring Materials").

It is very important that the adhesive of this invention comprises species which contain in the backbone ester groups resulting from the reaction of a carboxylic acid with a phenolic hydroxyl group. The importance of these phenolic esters is that although they have adequate hydrolytic stability to withstand commonly encountered environmental conditions, they present high enough hydrolytic instability to break down in the presence of strong alkalis. For this breakdown to occur, the phenolic group should be in the backbone. The relative number of hydrolyzable phenolic ester bonds per unit weight of the polymer needed to accomplish a certain desirable etching rate, may vary depending on the cross-link density, the molecular weight of the polymer involved, the nature and structural configuration of different segments constituting said polymer, as well as other parameters, such as the etchant to be used, and the like. However, a person of ordinary skill in the art may easily and without undue experimentation determine an appropriate number of such bonds to incorporate in the structure.

The higher the cross-link density the higher the demand for phenolic ester groups to provide the same rate of etching. Also more than one hydroxyls in one benzene ring promote faster hydrolysis. Carboxylic acids to be used with the phenolic hydroxyl group to form an ester are preferred as compared to strong inorganic acids, regardless of whether they are free or attached to organic molecules, since strong acids produce ester bonds which are too easily hydrolyzable.

Depending on the above considerations, the equivalent weight of the phenolic ester bond (number of grams of total material to be cross-linked and/or extended corresponding to one mole of phenolic ester bond) may be selected in a range from 200 to 10,000, more preferably from 200 to 5,000, and even more preferably from 300 to 2,500.

The oligomers used as adhesives for the laminates of the present invention may be any type of adhesive structures as long as they contain an adequate number of phenolic ester groups to result in a desirable etch-rate. Thus, depending on the particular application and requirements, they may be preferably epoxy based and more preferably reactive oligoimide based. One basic advantage of both types of chemistries is that they do not liberate gases during cross-linking or extension, and they offer excellent adhesive properties. Adhesion is usually better in the case of well formulated epoxies, while thermal stability is considerably higher in the case of polyimides. The preferred compositions of reactive oligomers according to this invention contain di- or polyamines, usually either as extenders or as crosslinkers, which are carriers of the phenolic ester bonds.

The oligoimides of this invention should preferably have as a source of cross-linking acetylenic, ethylenic, or nadic terminal groups, and even more preferably they should have terminal groups of maleimide, itaconimide, or citraconimide.

A preferred oligomer which may serve as an etchable adhesive for the substrates and laminates of this invention, has a general formula:

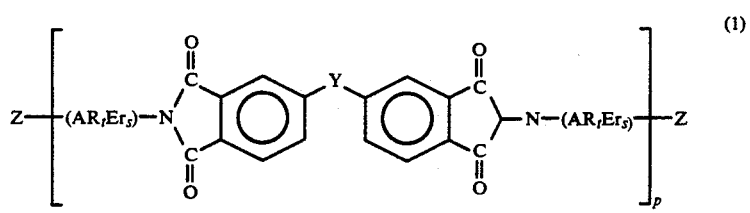

in which

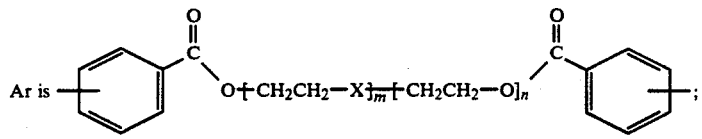

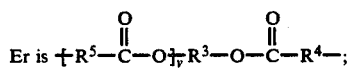

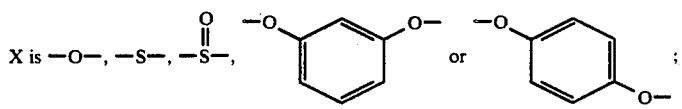

Y is —O—, 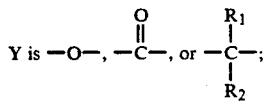

Z is 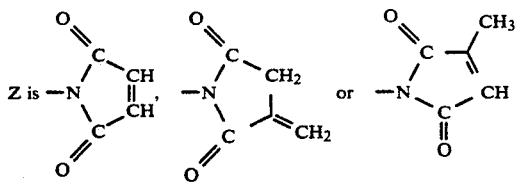

$R_1$ is —H, —$CH_3$, —$C_2H_5$ or —$CF_3$;
$R_2$ is —H, —$CH_3$, —$C_2H_5$ or —$CF_3$;
$R_3$ is a divalent radical having at least an aromatic portion through which it provides at least one of its two valencies.
$R_3$, $R_4$ and $R_5$ have molecular weights so that their sum is less than 2,000;
m is 0 to 1,
n is 0 to 1; so that m+n=1;
p is 0 to 15;
v is 0 to 1;
t is 0.95 to 0 and
s is 0.05 to 1, so that t+s=1
with the requirement that the crosslinked oligomer is chemically etchable, preferably in alkaline media.

A preferable final cured laminate comprises a metallic layer, an etchable polyimide layer, and an adhesive composition layer thereinbetween, the adhesive composition comprising a cross-linked reactive oligomer having in the backbone hydrolyzable phenolic ester groups and being of the formula

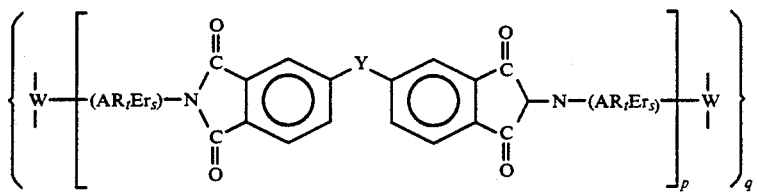

in which

Ar is 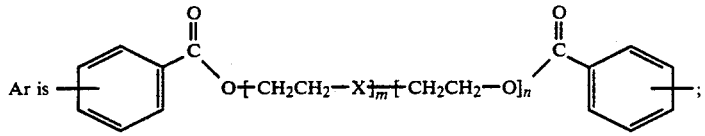

Er is 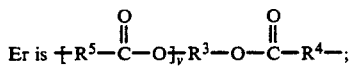

X is 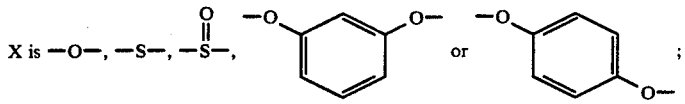

Y is —O—, 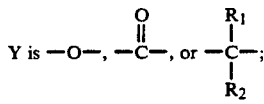

W is 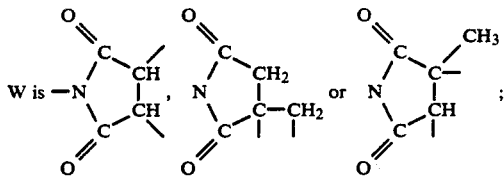

$R_1$ is —H, —$CH_3$, —$C_2H_5$ or —$CF_3$;
$R_2$ is —H, —$CH_3$, —$C_2H_5$ or —$CF_3$;
$R_3$ is a divalent radical having at least an aromatic portion through which it provides at least one of its two valencies;
$R_3$, $R_4$ and $R_5$ have molecular weights so that their sum is less than 2,000;
n is 0 to 1;
m is 0 to 1, so that m+n=1;
p is 0 to 15;
v is 0 to 1;
t is 0.95 to 0;

s is 0.05 to 1, so that t+s=1; and q is greater than 10

A material is generally chemically etchable when a chemical compound or a solution of a chemical compound may dissolve or disintegrate the material within a reasonable period of time, which in turn means that the rate of dissolution or disintegration, otherwise called etching rate, should be within practical limits. For the purposes of this invention the preferred chemical compounds or etchants for etching the adhesive and the dielectric or electrically insulating film are alkaline media such as, for example, aqueous or alcoholic solutions of sodium or potassium hydroxide, and a material is defined as etchable if it disintegrates in 1-50 cycles according to the method described in Example 1.

In general the etching rate depends on the type of the etchant, the concentration of the etchant, the temperature, and other parameters, such as, for example, pressure, if desired to be imposed. Thus, it is desirable to use a test with conditions as close as possible to the ones which will be used for etching these materials in the field.

For the purposes of this invention, it is preferable that the etching rate as measured by the method described in Example 1 is between 1 and 50 cycles, more preferably between 2 and 25 cycles, and even more preferably between 4 and 7 cycles. The rate of 4 to 7 cycles is the most preferable because it presents good accuracy combined with fast processing, and it also coincides with the etching rate of a number of polyimide films, such as, for example, Kapton ®. In general, however, it is very desirable to provide the adhesive with an etching rate in the vicinity of the etching rate of the dielectric or insulating film to be used with it. This is done to avoid overetching or underetching of one as compared to the other.

It is preferable that the different groups present in formula (1) be selected and combined in a manner that the oligomer possesses three important properties, among others, in addition to the aforementioned requirement of chemical etchability.

Thus, the oligomer should preferably (a) have a flow temperature, at which it flows, as explained below;

(b) have a curing temperature, higher than the flow temperature, at which it cross-links and becomes insoluble in polar solvents, (c) be soluble in a polar solvent at a temperature lower than the curing temperature.

It is preferable, as aforementioned, that the reactive oligomer flows at a temperature lower than the curing temperature, at least under pressure, thus behaving as a thermoplastic material. This flowability promotes wetting and better adhesion before the cure renders the oligomer intractable. The temperature range at which the reactive oligomer should flow is preferably between 100° C. and 220° C., and more preferably between 130° C. and 200° C. If the reactive oligomer flows at a temperature considerably lower than 100° C., blistering may occur during lamination, while if it flows at temperatures in high excess of 200° C., curing may start taking place, hindering the flow. The pressure range is preferably between atmospheric pressure and 1,000 psi, and more preferably between atmospheric pressure and 300 psi.

The reactive oligomer flows at a certain temperature and under certain pressure if a dry powder of the oligomer placed between two polyimide films turns into a clear melt after it is pressed in a conventional heatable press, at said temperature and pressure for half an hour. Under flow conditions, the oligomer may also be applied as an extruded coating.

It is preferable that in addition to being etchable, the reactive oligomer has a curing temperature, at which it cross-links, and thus it becomes insoluble in polar solvents. Insolubility of the cross-linked oligomers in polar solvents promotes better durability and insensitivity to weather and other adverse conditions. In addition, the increase in molecular weight, due to cross-linking, strengthens the structural configuration of the adhesive, and thus it increases the cohesive strength, by removing brittleness and providing better flexibility.

The cross-linked oligomer is insoluble in polar solvents if it is insoluble in solvents selected from the group consisting of sulfoxides, formamides, acetamides, N-alkyl-pyrrolidones, ketones, and mixtures thereof, at least at temperatures lower than the curing temperature.

It is preferable for the oligoimides of this invention that their curing temperature is higher than 200° C. and lower than 350° C., and more preferable higher than 230° C. and lower than 300° C. If the curing temperature is lower than 200° C., premature curing may interfere with a lamination process in which the reactive oligomer of the present invention may be used, as it is discussed at a later section, while if the curing temperature is considerably higher than 350° C., appreciable thermal/oxidative degradation may take place, which in turn may have detrimental consequences on the performance of the cured oligomer. In addition, if copper is present it will oxidize excessively, unless curing is taking place in inert atmosphere, which is very expensive and therefore, undesirable; blistering may also occur. Further, it is always preferable to be able to cure at as low a temperature as possible for energy conservation. At these temperatures, the oligomer of this invention behaves as a thermoset material.

Preferably, the difference between the curing temperature of an oligomer of this invention and the flow temperature should be greater than 10° C., more preferably greater than 20° C., and even more preferably greater than 40° C. Under these conditions, the reactive oligomer of this invention behaves initially as a thermoplastic material, while it behaves as a thermoset material at more elevated temperatures.

A way to determine with good accuracy the melting point as well as the curing temperature of the reactive oligomers of this invention is by Differential Scanning Calorimetry (DSC). The melting point as determined by this technique may also be an approximation of the flow temperature determined as described earlier.

It is further desirable that the reactive oligomer is substantially soluble in at least one polar solvent, including any suitable mixture of solvents, when heated at a temperature between the flow temperature and the curing temperature for ½ hour, and then brought to room temperature. This is because it is highly preferable to apply adhesive layers of the reactive oligomers of this invention from solution rather than in the form of powders and the like. By being soluble it is meant that a major portion representing more than 95% by weight of the reactive oligomer under consideration comes to clear solution.

The solution should be flowable and suitable for application preferably at room temperature, when the content in dissolved reactive oligomer is preferably higher than 5%, more preferably higher than 10%, and even more preferably higher than 20% by weight.

Preferably the reactive oligomer dissolved as discussed above, remains in solution for extended periods of time. Thus, it is preferable that the reactive oligomer remains in solution for more than 24 hours, more preferably more than 15 days, and even more preferably more than one month, when maintained at room temperature. If the reactive oligomer solution is kept in the refrigerator, these periods are extended considerably. However, it is commercially undesirable and expensive to store and handle materials at temperatures lower than room temperature.

The applicant suggests, without any implication as to restrict the scope of this invention, that reactive oligomer molecules having a higher regularity than a certain critical value, and easier alignment characteristics, crystallize with time and come out of solution.

It is preferable that the polar solvent in which the reactive oligomer is soluble is selected from the group consisting of a sulfoxide, a formamide, an acetamide, N-alkyl-pyrrolidone, a ketone, and mixtures thereof. From these groups of solvents, N-methyl-2-pyrrolidone is preferable.

The main function of the Ar group is to provide flexibility, while the main function of the Er group is to provide chemical etchability. The size of the different segments or radicals of the Er groups should be selected such that no excessively high molecular weights are attained by the oligomer. The molecular weight of the reactive oligomer is of high importance, since comparatively high molecular weights decrease drastically the usable concentration of reactive oligomer in a solvent, or raise excessively the viscosity, and they also decrease the cross-link density resulting in inferior properties of the finally cross-linked oligomer adhesive. Thus, in addition of selecting the different segments of Er to be rather small, it has been found that p, which may be a measure of molecular weight, should be kept preferably between 0 and 15, more preferably between 3 and 10, and even more preferably between 4 and 8.

Regarding the Ar group, the following comments may be made.

Although the nitrogen atom of the Z group in Formula (1) may be connected in any position of the terminal benzene rings of the Ar group, the meta-position is preferable as contributing higher flexibility when compared to the para-position. The ortho-position would give very unstable structures, if any, due to steric hindrance.

The values of m and n should be in the region of 1 to 0, with the requirement that $m+n=1$. Considerably higher values would detract from thermal/oxidative stability, while a value of 0 for both would increase the flow temperature excessively.

The ether-functionality providing entity —X— may take a number of different forms, as shown in Formula (1), with preference to —O—$C_6H_4$—O—.

—Y— may also take a number of different forms, with —$C(CF_3)_2$—, at least partially, being the preferred form, since it provides a number of advantages, including considerable extension of solution shelf-life, and lower dielectric constant. For economic reasons, however, one might prefer to use structures where —Y— is mainly —CO—, with an adequate amount of structures where —Y— is —$C(CF_3)_2$— (preferably at least 10 mole % and more at least 25 mole %), so that the shelf-life of the final product solution is extended to a desired level.

Considering now the Er group, $R^3$, $R^4$, and $R^5$ should be small enough, so that the sum of their molecular weights does not exceed preferably 2,000, more preferably 1,000, and even more preferably 500.

It is important that at least one, and preferably both oxygens connected to the $R^3$ radical, are linked through an aromatic portion of the $R^3$ radical. In other words, it is of importance that the ester linkages are formed by a phenolic hydroxyl group in order to have an appropriate degree of hydrolytic instability to render the polymer etchable to strongly alkaline environments without deteriorating their hydrolytic stability in commonly encountered environments. Regarding the acid component which has produced the ester, it is preferable that it is a carboxyl group, since stronger acid groups, such as, for example, sulfuric or sulfonic, result usually in excessively hydrolytically-unstable esters. The acid groups may be connected to the radicals $R^4$ and $R^5$ through either aliphatic or aromatic entities. However, preferably all three $R^3$, $R^4$, and $R^5$ are substantially aromatic to enhance heat stability. Also, preferably the value of v may be between 0 and 1, and even more preferably 1.

Bisphenol A and hydroquinone are preferred examples of the source for $R^3$, while resorcinol is even more preferred as having two hydroxyl groups in the benzene ring, and thus the phenolic ester bonds it may form are more readily hydrolyzable. It should, however be stressed that the sources of the different radicals are limited by the claims only, while the above examples constitute only preferences. Thus, radicals with only one phenolic hydroxyl group may also be used for the esterified phenolic ester group.

The value of t should preferably be between 0.95 and 0, while the value of s should preferably be between 0.05 and 1, respectively, in a manner that $t+s=1$. It should be understood, however, that these values represent only mole averages, and that what is shown in formula (1) as —(ArsErt)— will in fact be either —Ar— or —Er— in each individual molecule.

—Z— may be provided in the form of maleimide, itaconimide, citraconimide, or mixtures thereof, the preferable being maleimide. The double bonds of these groups open and react with each other to cross-link the reactive oligomer at a range of temperatures between 230° C. and 300° C.

Diamines may also be used to extend the reactive oligomers of the present invention by Michael addition, the preferable diamines for this purpose being ones having the general formula $H_2N$—Ar—$NH_2$, or $H_2N$—Er—$NH_2$, or chemical or physical mixtures thereof, where —Ar— and —Er— have the structures defined above. Although the cross-link density due to double bonds decreases by the extension with the diamine, further reaction of the formed secondary amine with remaining double bonds provides additional cross-linking at curing temperatures. Adhesives of good properties may be obtained even in the case where $p=0$, and an oligomer of the formula Z—Ar—Z or Z—Er—Z is extended with a diamine having the formula $H_2N$—Er—$NH_2$ or $H_2N$—Ar—$NH_2$, respectively. More rigid diamines require higher values for p. The most preferred diamine to represent Ar, however, is hydroquinone-bis[2-(3-aminobenzoyloxy)ethyl]ether, and the most preferred diamine to represent Er is resorcinol bis(3-aminobenzoate).

The reactive oligomers of this invention may be prepared by conventional techniques, well known in the art.

For example, a diamine having a formula $H_2N-Ar-NH_2$, which may be prepared as indicated in Example 2, or which may be commercially available, and a diamine having a formula $H_2N-Er-NH_2$, which may be prepared as indicated in Example 3, are reacted with a dianhydride having the formula $O(CO)_2-C_6H_3-Y-C_6H_3-(CO)_2O$, in the desired molecular proportions, wherein —Ar—, —Er—, and —Y— have the same definitions as in Formula (1), yielding an oligomeric amic acid. In sequence, maleic, or itaconic, or citraconic anhydride, or a mixture thereof is added, followed by addition of an excess of a water scavenger, such as, for example, acetic anhydride, in order to form an oligomer of the present invention in crude form. A catalyst, such as a tertiary amine may also be used. The reactive oligomer is then precipitated, rinsed, and dried to obtain its purified form.

Application of the reactive oligomer solution can be accomplished in any number of ways, such as by slit die, dipping or kiss-roll coating, followed by metering with doctor knife, doctor rolls, squeeze rolls or air knife. It may also be applied by brushing or spraying.

Using such techniques, it is possible to prepare both one- and two-side coated structures. In preparation of the two-side coated structures, one can apply the coatings to the two sides either simultaneously or consecutively before going to the drying and curing stage.

The reactive oligomer adhesive may be coated on a polyimide base film or on a metal substrate. The coating thickness may vary preferably between 2 and 50 micrometers, and more preferably between 10 and 30 micrometers.

The polyimide base film may be used as is, or it may be prepared by either a chemical or thermal conversion process and may be surface treated, e.g., by chemical etching, corona treatment, laser etching etc., to improve adhesion.

A single polyimide metal-clad of the present invention comprises a reactive oligomer layer which adheres to a metal foil such as a copper, aluminum, nickel, steel or an alloy containing one or more of these metals as a substantial constituent, or to a foil of amorphous metal. The reactive oligomer layer adheres firmly to the metal and has a peel strength of 3 pli or higher. The metals do not have to be used as elements in pure form, i.e., it is also possible to use substrates of metal alloys, such as alloys containing nickel, chromium or iron or nickel and copper, or of amorphous alloys containing iron. Particularly suitable metallic substrates are foils of rolled, annealed copper alloy, In many cases, it has been proven to be of advantage to pretreat the metallic substrate before coating. The pretreatment, if used, may consist of chemical treatment or a mechanical roughening treatment. This pretreatment enables the adhesion of the reactive oligomer layer and, hence, the peel strength to be further increased. Apart from roughening the surface, the chemical pretreatment may also lead to the formation of metal oxide groups, which may enable the adhesion of the metal to the copolyimide later to be further increased.

A polyimide multi-clad of the present invention compromising a double side copper clad may be prepared by laminating copper foil to both sides of an adhesive coated dielectric polyimide film. The construction can also be made by laminating adhesive coated copper foil to both sides of a dielectric polyimide film or to an adhesive coated dielectric polyimide film.

Roll clads may also be made by continuous lamination of the adhesive coated dielectric film to copper foil using a high temperature double belt press or a high temperature nip roll laminator.

In general, the preferred method for making a laminate of a first film and a second film, at least in the cases where a reactive oligoimide is used as an adhesive, comprises a number of steps.

The initial step is to coat the first film with a solution of a reactive oligomer in a polar solvent, according to this invention. The coated film is then optionally heated to a first temperature lower than the flow temperature (provided the oligomer is flowable) of the reactive oligomer, in order to remove most of the solvent from the reactive oligomer coating, and then it is subjected a second temperature, between the flow temperature and the curing temperature, in order to cause the reactive oligomer to flow and substantially remove all the solvent from the reactive oligomer coating. The second film is then placed against the reactive oligomer coating, thus forming a sandwich, and pressure is applied to the sandwich at a third temperature, again between the flow temperature and the curing temperature of the reactive oligomer, in order to form an uncured laminate. The second and the third temperatures may be the same or different. The uncured laminate may then be cured and form a cured laminate, by subjecting it to the curing temperature, in the press or out of the press. Preferably one of the first and the second films is copper and the other is polyimide.

In the cases where epoxies are used as reactive oligomers along with a polyamine containing phenolic ester groups, it is preferable that the formulation used is liquid and solventless.

The clad of a copper layer, for example, on a polyimide film, adhered to each other by an oligoimide of this invention, may be etched through imaged photoresist layers to result in circuitry containing copper conductors with etched interconnecting vias and other holes by well established techniques in the Electronics Industry.

The polyimide base films used in the laminates of the invention are preferably about 0.3 to 5 mils in thickness and can be obtained from polyamic acid precursors derived from the reaction of suitable diamines with suitable dianhydrides in the manner described in, for example, U.S. Pat. No. 3,179,614.

The above discussion has been mainly directed to the use of oligoimides, which are the preferred oligomers for the laminates of the present invention. When epoxies or other oligomeric species are used, the conditions of treating them should comply to their specifications.

Diamines having phenolic ester groups in their backbones are the preferred species bearing hydrolyzable bonds in both cases of both epoxies and oligoimides, as exemplified in a later section.

Examples of dianhydrides which may be used in the polyimide base film include:
pyromellitic dianhydride;
3,4,9,10-perylene tetracarboxylic dianhydride;
naphthalene-2,3,6,7-tetracarboxylic dianhydride;
naphthalene-1,4,5,8-tetracarboxylic dianhydride;
bis(3,4-dicarboxyphenyl) ether dianhydride;
bis(3,4-dicarboxyphenyl) sulfone dianhydride;
2,3,2',3'-benzophenonetetracarboxylic dianhydride;
bis(3,4-dicarboxyphenyl) sulfide dianhydride;

bis(3,4-dicarboxyphenyl) methane dianhydride;
2,2-bis(3,4-dicarboxyphenyl) propane dianhydride;
2,2-bis(3,4-dicarboxyphenyl) hexafluoropropane;
3,4,3',4'-biphenyltetracarboxylic dianhydride;
2,6-dichloronaphthalene-1,4,5,8-tetracarboxylic dianhydride;
2,7-dichloronaphthalene-1,4,5,8-tetracarboxylic dianhydride;
2,3,6,7-tetrachloronaphthalene-1,4,5,8-tetracarboxylic dianhydride;
phenanthrene-1,8,9,10-tetracarboxylic dianhydride;
pyrazine-2,3,5,6-tetracarboxylic dianhydride;
benzene-1,2,3,4-tetracarboxylic dianhydride; and
thiophene-2,3,4,5-tetracarboxylic dianhydride.

Examples of diamines which may be used together with the dianhydrides in the polyimide base film include the following:
meta-phenylenediamine;
para-phenylenediamine;
2,2-bis(4-aminophenyl) propane;
4,4'-diaminodiphenylmethane;
4,4'-diaminodiphenyl sulfide;
4,4'-diaminodiphenyl sulfone;
3,3'-diaminodiphenyl sulfone;
4,4'-diaminodiphenyl ether;
2,6-diaminopyridine;
bis(3-aminophenyl) diethyl silane;
benzidine;
3,3'-dichlorobenzidine;
3,3'-dimethoxybenzidine;
4,4'-diaminobenzophenone;
N,N-bis(4-aminophenyl)-n-butylamine;
N,N-bis(4-aminophenyl) methylamine;
1,5-diaminonaphthalene;
3,3'-dimethyl-4,4'-diaminobiphenyl;
m-aminobenzoyl-p-aminoanilide;
4-aminophenyl-3-aminobenzoate;
N,N-bis(4-aminophenyl) aniline;
2,4-bis(beta-amino-t-butyl) toluene;
bis(p-beta-amino-t-butylphenyl) ether;
p-bis-2-(2-methyl-4-aminopentyl) benzene;
p-bis(1,1-dimethyl-5-aminopentyl) benzene;
m-xylylenediamine;
p-xylylenediamine;
position isomers of the above, and mixtures thereof.

The preparation of polyimides and polyamic acids is more fully described in U.S. Pat. No. 3,179,614 and U.S. Pat. No. 3,179,634.

A particularly preferred polyimide base film is derived from 4,4'-diaminodiphenyl ether and pyromellitic dianhydride.

GLOSSARY

BMI: Bismaleimide
BPA-DEDA: bisphenol A diester diamine {bisphenol A bis(3-aminobenzoate)}
BTDA: Benzophenone tetracarboxylic acid dianhydride
DEDA: Diester diamine
DMAC: Dimethylacetamide
DMF: Dimethylformamide
6FDA: 2,2'-bis(3,4-dicarboxyphenyl)-hexafluoropropane
g: Gram
HQ-BABEE: Hydroquinone-bis[2-(3-aminobenzoyloxy)-ethyl]ether
HQ-BNBEE: Hydroquinone-bis[2(nitrobenzoyloxy)-ethyl]ether
MDA-BMI: Bismaleimide of methylene dianiline
ml: milliliter
NMP: N-methyl 2-pyrrolidone
QUATREX 1010: Electronic Grade Resin, Reaction Product of epichlorohydrin with bisphenol A, having an epoxy equivalent weight of 200, from Dow Chemical, U.S.A.
R-DEDA: Resorcinol diester diamine {resorcinol bis(3-aminobenzoate)}
R-DEDA-BMI: Bismaleimide of resorcinol-1,3-bis(3-aminobenzoate)

All parts and percentages are by weight unless otherwise indicated.

EXAMPLE 1

Method for Checking Etching Properties

The material to be tested is made in the form of a film having dimensions of 4 cm×2.5 cm×50 micrometers. In the case the material is in solution, the solution is doctored on an aluminum foil. After solvent evaporation, the film is cured, stripped from the aluminum foil and cut into 4 cm×2.5 cm pieces. The thickness of the doctored solution should be high enough to result in a cured film of substantially 50 micrometers.

The cut pieces are hung on clips and they are alternated in a solution of containing 13% potassium hydroxide, 11% distilled water, and 76% ethanol at 60° C. for 1 minute under stirring, and in a bath of deionized water at 60° C. for 30 seconds, also under stirring. One submersion in the potassium hydroxide solution followed by submersion to the deionized water, constitutes one cycle.

LF020 Kapton® film (2 mil thick polyimide film, available from Du Pont, Wilmington, Del.) serves as a control, and it disintegrates in 5–6 cycles.

The film is defined as chemically etchable if it disintegrates in 1 to 50 cycles.

EXAMPLE 2

Preparation of hydroquinone-bis[2(aminobenzoyloxy)-ethyl]ether (HO-BABEE)

In a 5-liter flask, fitted with mechanical stirrer, thermometer, nitrogen inlet, and condenser topped with a calcium sulfate drying tube, there were dissolved 426 g (2.15 moles) of hydroquinone-bis (2-hydroxyethyl)ether (from Aldrich Chemical) in 1800 ml DMAC and 750 ml pyridine. To the stirred solution there were added in small portions 800 g (4.3 moles) of 3-nitrobenzoyl chloride (from Aldrich Chemical) at a rate that the reaction temperature did not exceed 80° C. The mixture was stirred at 70°–75° C. for 3 hours during which solids began to separate. The mixture was cooled to room temperature and poured into stirred methanol, maintained cold by addition of ice cubes. The precipitated dinitro-diester compound was collected by suction filtration and rinsed with copious amounts of water to remove solvents and salts. After a rinse with cold methanol the product was air dried as much as possible while still in the funnel, then vacuum dried overnight at 110° C. The yield of HQ-BNBEE, m.p. 169°–171° C., was 1020 g (96%).

Equally good product in excellent yields is obtained by conventional esterification of the ethoxylated hydroquinone used above with 3-nitrobenzoic acid in xylene solvent in presence of methanesulfonic acid catalyst.

The reaction is completed when the theoretical amount of water has been collected using a Dean Stark trap.

The dinitro compound (hydroquinone-bis[2(nitrobenzoyloxy)-ethyl]ether) described in Example 1 was hydrogenated to the corresponding diamine by initially charging 180 g of the compound in a 1000 ml shaker tube along with 600 ml of DMAC, and 5 g catalyst (10% Pd on carbon), followed by charging hydrogen at 500 psig until there was no further pressure drop. The reduction mixture was heated to dissolve separated solids, filtered to remove carbon and catalyst, then poured into a stirred, ice-cold methanol/water mixture causing precipitation of a slightly yellow diamine. The latter was collected by suction filtration, rinsed with water and cold methanol; then vacuum dried overnight at 110° C. The yield of HQ-BABEE, melting at 139°-141° C., was practically theoretical.

Elemental Analysis

Calculated for $C_{24}H_{24}O_6N_2$: C, 66.04; H, 5.56; O 22.00; N, 6.42; found: C, 65.92; H, 5.53; O, 22.27; N, 6.28

EXAMPLE 3

Preparation of Resorcinol Bis (3-Aminobenzoate) (R-DEDA)

In a 3-liter flask, fitted with mechanical stirrer, thermometer, nitrogen inlet and condenser topped with a calcium sulfate drying tube, were charged 209 g (1.89 moles) resorcinol, 700 ml dimethylacetamide (DMAC) and 700 ml pyridine, both having been predried over molecular sieves. To the stirred solution there were added 700 g (3.77 moles), in 7 portions of 100 g, of 3-nitrobenzoylchloride at rates that raised the internal temperature to 85°-90° C. The mixture was stirred at those temperatures for 2 hours, then cooled to ambient levels and poured in 3 liters methanol that had been cooled to 10°-15° C. by addition of ice cubes. The precipitated diesterdinitro compound, resorcinol bis(3-nitrobenzoate), was collected by suction filtration, rinsed several times with water, once with ice-cold methanol, air-dried as much as possible on the funnel with continued suction, then in a vacuum oven overnight at 110° C. The yield of resorcinol bis(3-nitrobenzoate), m.p. 177°-178° C., was 731 g (95%).

Approximately 184 g (0.45 mole) of the above dinitro compound was reduced in an autoclave at ambient temperature under 500 psig hydrogen pressure in presence of 500 ml DMAC and 3 g of 10% palladium-on-carbon catalyst until there was no further hydrogen absorption. The mixture was filtered to remove carbon and catalyst and the clear filtrate was poured in stirred, ice-cold methanol/water mixture until precipitation was complete. The resorcinol bis(3-aminobenzoate) was collected by suction filtration, rinsed with water, then with cold methanol, and vacuum dried overnight at 110° C. The yield of resorcinol bis(3-aminobenzoate) (R-DEDA), m.p. 139°-140° C., was 155 g (theoretical). After one recrystallization from 95% ethanol, the pure diesterdiamine had a melting point of 141°-143° C.

Elemental Analysis:

Calculated for $C_{20}H_{16}N_2O_4$: C, 68.95; H, 4.63; N, 8.04; O, 18.37; found: C, 68.89; H, 4.89; N, 7.96; O 18.06

EXAMPLE 4

Preparation of Bisphenol-A Bis (3-aminobenzoate)

In a 2 liter round-bottom, 4-neck flask fitted with mechanical stirrer, thermometer, nitrogen inlet and condenser connected to a bubbler, there were charged 184 g (1.1 mole) meta-nitrobenzoic acid and 400 ml dimethylformamide (DMF). To the stirred solution there were added 119 g (1.0 mole) thionyl chloride and stirred for 2 hours (to convert the acid in situ to the corresponding acid chloride), the mildly exothermic reaction resulting in rise of temperature to 47°-50° C. To the stirred acid chloride solution there were added in one portion 102 g (0.45 mole) of 4,4'-isopropylidenediphenol (bisphenol A) causing the temperature to rise to about 75° C. While providing minimal cooling, 400 ml pyridine were added in portions and at rates preventing the temperature from exceeding 80° C. The mixture was stirred at 80° C. for 3 hours, then cooled to room temperature and poured in ice-cold methanol. The product, light cream-colored, was collected by suction filtration. After rinsing once with methanol, 3 times with water and once again with methanol, the dinitrodiester compound was dried at 110° C. overnight. Yield: 229 g (97% on the bisphenol).

About 180 g of the above precursor was reduced in an autoclave at room temperature under 500 psig of hydrogen pressure in presence of 400 ml dimethylacetamide (DMAC) and 3 g of 10% palladium-on-carbon catalyst. The reaction mixture (product in solution) was filtered to remove catalyst and carbon and the filtrate was transferred to a 3-liter beaker with provisions for stirring. Ice cubes were added slowly with stirring until there was no more visible precipitation of product. The diester-diamine (BPA-DEDA) was collected by suction filtration, rinsed with water to remove as much DMAC as possible, then twice with ice-cold methanol, followed by vacuum drying on the funnel under continued suction and nitrogen blanket, then overnight at 110° C. in a vacuum oven. Yield: 149 g (89%), m.p.181°-182° C.

EXAMPLE 5

6FDA (4) //HQ-BABEE (5)-BMI

In a predried (flame) one-liter 4-neck flask fitted with thermometer, mechanical stirrer, inlet for dry nitrogen and outlet connected to a bubbler (to monitor nitrogen flow), there were placed 43.6 g (0.1 mole) HQ-BABEE and 300 ml NMP that had been dried over molecular sieves. The mixture was stirred at ambient temperatures until all the diamine had dissolved while maintaining a gentle nitrogen flow. To the stirred solution there were added in one portion 35.5 g (0.08 mole) 6FDA causing the internal temperature to rise to about 40° C., and the solution viscosity to increase. The mixture was stirred at room temperature for 3.5 hours, at the end of which time 5.7 g (0.055 mole) maleic anhydride was added. Stirring was continued for 3 hours to allow for reaction of maleic anhydride with the amine end groups of the condensation oligomeric amic acid. To the stirred mixture, there were added in quick succession 40 ml acetic anhydride, 10 ml triethylamine and 2 g anhydrous sodium acetate and stirring was continued for 4 hours. The solution was poured into stirred deionized water and the precipitated yellow reactive oligomer was collected by suction filtration. After several rinses with deionized water and one rinse with methanol the soft flake was dried overnight under vacuum at 110° C.

The above reactive oligomer flows in the range of 140°-200° C., and it is not etchable after it is cured. It dissolves in NMP to make solutions containing more than 40% reactive oligomer by weight. These solutions have very long shelf life (>2 months).

The oligomer after cure is not etchable, when tested according to the method described in Example 1.

EXAMPLE 6

6FDA (9) //HO-BABEE (10)-BMI

The experimental set up and the overall procedure were the same as in Example 5, with the difference of reagent amounts as shown below:
HQ-BABEE: 43.6 g (0.1 mole)
6FDA: 40 g (0.9 mole)
NMP: 334 ml
Maleic anhydride: 3 g (0.03 mole)
Acetic anhydride: 40 ml
Triethylamine: 10 ml
Anhydrous sodium acetate: 2 g.

This higher molecular weight reactive oligomer still flowed at 170°-200° C., dissolved in NMP (>35%), and solutions were very stable. The oligomer after cure is not etchable, when tested according to the method described in Example 1.

EXAMPLE 7

BTDA (4) //HO-BABEE (5)-BMI

The reaction set up and procedure were the same as in Example 5.

In the flask, there were placed 43.6 g (0.1 mole) HQ-BABEE and 280 ml NMP. To the stirred solution, there were added 25.8 g (0.08 mole) BTDA in one portion, and stirred for 3.5 hours. In sequence, 5.7 grams of maleic anhydride were added, and the mixture was stirred for 3 hours as in Example 5. All other reagents (for imidization) were the same and in the same amounts as in Example 5. Precipitation and purification again was the same as in Example 5.

NOTE: 35% solutions in NMP could be used the same date and give excellent lamination/adhesion results. However, reactive oligomer crystallizes out after storage at room temperature for about 24 hours. More dilute solutions (25% have somewhat longer shelf life, up to 3 days). Shelf life can be extended further by storing at low temperatures, which is still rather inconvenient.

The flake produced this way flows in the 160°-200° C. range as above. The oligomer after cure is not etchable, when tested according to the method described in Example 1.

EXAMPLE 8

BTDA (3) / 6FDA (1) //HO-BABEE (5)-BMI

This example demonstrates that the shelf life of an oligomer such as the one described in Example 7, may increase considerably by replacing part of the BTDA with 6FDA. Set up, procedure and reagents were the same as in Example 7, except as indicated below.

43.6 g (0.1 mole) of HQ-BABEE were dissolved in 300 ml NMP. To this, there were added 19.3 g (0.06 mole) BTDA and 8.9 g (0.02 mole 6FDA). Everything else was the same as in Example 7.

The flake produced in this manner flows in the same range of 160°-200° C., but solution shelf life appears to be as good as that of the reactive oligomers made by using exclusively 6FDA.

The oligomer after cure is not etchable, when tested according to the method described in Example 1.

EXAMPLE 9

Lamination and Adhesion Results

A 35% solution of BTDA (4) /HQ-BABEE (5)-BMI in NMP was used to coat brass-treated copper (commercially designated as ED copper) using a doctor's knife at 5 mil wet clearance. The coated sheets were placed in a convection oven at 160° C. for about one hour to remove NMP. Copper plus adhesive was then laminated onto LF020 Kapton ® film (2 mil thick polyimide film, available from E. I. du Pont de Nemours and Company, Wilmington, Del.) at 170° C. and 200 psi for 30 minutes, followed by cooling to 75° C., while maintaining 200 psi pressure. The laminates were then cured by placing them in the same oven for 30 minutes at 240° C., and then for one hour at 280° C. There were no visible blisters or bubbles.

Peel strength was determined by using 0.5" strips, and pulling the copper and Kapton ® films apart (I.P.C. Standard Method 2.4.9, "Peel Strength, Flexible Printed Wiring Materials"). In all instances the Kapton ® film broke at about 9.5 pli (Pounds per Linear Inch), which means that the peel strength was better than 9 pli.

EXAMPLE 10

A. Preparation of (HO-BABEE-BMI)

In a one-liter flask fitted with mechanical stirrer, thermometer and inlet/outlets for nitrogen, there were placed 43.6 g (0.1 mole) of the above diamine and 200 ml N-methyl pyrrolidone (NMP). The mixture was stirred at ambient temperature until all the diamine had dissolved and 24.5 g (0.25 mole) maleic anhydride was added causing temperature to rise to about 40°-45° C. The mixture was stirred (cooling on its own) for 1.5 hours at ambient temperatures. At the end of that time, 45 ml of acetic anhydride and 2.5 g anhydrous sodium acetate were added, and the mixture was stirred at ambient temperature for 3 hours to affect imidization. The mixture was poured in water under stirring, and the precipitated bismaleimide was collected by suction filtration. After several rinses with water the product was dried on the funnel as much as possible with continued suction, and then overnight at 90° C. under vacuum. The cream-colored powder melted at 135°-137° C.

B. "Michael Addition" of HO-BABEE-BMI with HO-BABEE

Three different mixtures of the above BMI with HQ-BABEE diamine were prepared as follows:

(1) 6.0 g HQ-BABEE-BMI, 4.4 g HQ-BABEE (1:1 molar ratio) and 10.4 g NMP, i.e., 50% solids.

(2) 6.0 g HQ-BABEE-BMI, 3.2 g HQ-BABEE (4/3 molar ratio) and 9.2 g NMP, i.e., 50% solids.

(3) 6.0 g HQ-BABEE-BMI, 2.2 g HQ-BABEE (2/1 molar ratio) and 8.2 g NMP, i.e., 50% solids.

These mixtures were heated to about 60° C., and then to 120° C. for about one hour, resulting in homogeneous solutions, followed by cooling to ambient temperatures.

C. Lamination

The above solutions were used to laminate a copper film to a polyimide film, in the same manner as described in Example 8. Evaluation of peel strength gave the following results:

(1) 3 pli;
(2) 4.7 pli; and (3) 3.8 pli.

D. Etching Evaluation

Cured films made from the above solutions are not etchable according to the method of Example 1.

EXAMPLE 11

Preparation of 6FDA (4) //HO-BABEE (4) /R-DEDA (1)-BMI

In a predried one-liter, 4-neck flask fitted with mechanical stirrer, thermometer, and inlet/outlet for maintaining a nitrogen atmosphere, were placed 34.9 g (0.08 mole) HQ-BABEE, 6.9 g (0.02 mole) R-DEDA and 300 ml NMP. The mixture was stirred at ambient temperatures until all solids had dissolved and 35.5 g (0.08 mole) 6FDA was added in one portion. The internal temperature rose to about 35° C. but cooled slowly on its own to room temperature. After stirring for 4 hours, 5.7 g (0.58 mole) maleic anhydride was added and the mixture was stirred for another 4 hours at ambient temperatures. To imidize the bismaleamic acid-capped oligomer, 45 ml acetic anhydride was added in one portion, followed by 22 ml triethylamine and 2.5 g anhydrous sodium acetate. The mixture was stirred for 5 hours, then poured in stirred deionized water resulting in precipitation of a yellow, brittle flake. The flake was collected by suction filtration, rinsed several times with deionized water to remove solvent an excess reagents, rinsed once with methanol, air-dried as much as possible with continued suction while on the funnel, then vacuum-dried overnight at 110° C.

The dry flake softens at 160° C. and melts completely in the 170°-200° C. range.

Free films of this adhesive, when tested according to the method described in Example 1, disintegrate in 5-6 cycles.

EXAMPLE 12

Preparation of BTDA (4) //HO-BABEE (4)/R-DEDA (1)-BMI

Equipment, procedure and reagents, as well as amounts were the same as in Example 11 except that BTDA in the amount of 25.8 g (0.08 mole) was used instead of 6FDA. The yellow flake melt-flowed in the same range as the preceding oligomer.

Lamination and adhesion results using solutions from this case to laminate a copper film on a polyimide film, as in the case of Example 9, showed a peel strength of about 5.5-6.5 pli.

Free films of this adhesive, when tested according to the method described in Example 1, disintegrate in 5-6 cycles.

EXAMPLE 13

Preparation of BTDA (4) //HO-BABEE (3)/R-DEDA (2)-BMI

Equipment an procedure were the same as in Example 4. Charges were made as follows: HQ-BABEE, 26.2 g 0,06 mole, and R-DEDA, 13.9 g (0.02 mole) were charged and dissolved in 265 ml NMP. To the stirred solution there were added 25.8 g (0.08 mole) BTDA in one portion, and the mixture (mildly exothermic) was stirred for 4 hours at room temperature. Maleic anhydride, 5.7 g, was added and the mixture was stirred for 4 hours. Acetic anhydride, triethylamine and sodium acetate were added in the same amounts as in Example 11, allowing 5-hour imidization time with continued stirring. The precipitated and dried flake melt-flowed in the 180°-210° C. range.

Lamination and adhesion results using solutions from this case to laminate a copper film on a polyimide film, as in the case of Example 9, showed a peel strength of about 5.5-6.5 pli.

Free films of this adhesive, when tested according to the method described in Example 1, disintegrate in 2-3 cycles.

EXAMPLE 14

Preparation of BTDA (4) //HO-BABEE (4)/BPA-DEDA (1)BMI

Equipment and procedure were the same as in Example 11. The following were charged into the one-liter flask: HQ-BABEE, 34.9 g (0.08 mole), BPA-DEDA, 9.3 g (0.02 mole) and 300 ml NMP. To the stirred solution there were added 25.8 g (0.08) mole BTDA as usual. After 4 hours, 5.7 g maleic anhydride was added and stirred for 4 hours. Imidization was accomplished by charging 45 ml acetic anhydride, 22 ml triethylamine and 2.5 g anhydrous sodium acetate and stirring for 5 hours. Precipitation, filtration, washing and drying were carried out as above.

Melt-flow was comparable to that of Example 11. However, wet-etch tests conducted as described in Example 1, showed that films from this oligomer required in excess of 20 cycles before they disintegrated.

EXAMPLE 15

Preparation of BTDA (4) //HO-BABEE (3) /BPA-DEDA (2)-BMI

Same equipment and procedure as usual. Reagents: HQ-BABEE, 26.2 g (0.06 mole), BPA-DEDA, 18.6 g (0.04 mole) in 280 ml NMP. To the stirred solution there were added 25.8 g (0.08 mole) BTDA and stirring was continued for 4 hours. Maleic anhydride, 5.7, was added and stirred for 4 hours, followed by addition of acetic anhydride, 45 ml, triethylamine, 20 ml, and 2 g anhydrous sodium acetate, and stirring for 5 hours. Precipitation, filtration, washing and drying were carried out as usual.

Melt-flow was in the 190°-220° C. range, unlike its R-DEDA counterpart {BTDA(4)//HQ-BABEE(3)/R-DEDA(2)-BMI}, which melts at considerably higher temperatures. Cured films, wet-etched at about 5-6 cycles, according to the method described in Example 1.

EXAMPLE 16

Preparation of BTDA (4) //BPA-DEDA (5)-BMI

In the same reaction flask there were dissolved 46.6 g (0.1 mole) BPA-DEDA in 300 ml NMP. To the stirred solution there were added in one portion 25.8 g (0.08 mole) BTDA and stirring was continued for 4 hours. Maleic anhydride, 5.7 g, was added and the mixture was stirred at room temperature for another 4 hours. To imidize, acetic anhydride, 50 ml, was added along with 22 ml triethylamine and 2 g anhydrous sodium acetate, followed by 5-hour stirring at room temperature. Precipitation, filtration and drying were carried out as described in other examples above.

This oligomer is completely soluble in NMP at all concentrations, unlike BPDA(4)//R-DEDA(5)-BMI which is insoluble.

This oligomer disintegrates easily when tested with the method described in Example 1.

EXAMPLE 17

Michael Addition Chain Extension of HO-BABEE-BMI with R-DEDA

When 6 g (0.01 mole) of HQ-BABEE-BMI is mixed with 3.5 g (0.01 mole) R-DEDA in NMP (50% by weight) and heated with stirring at 120° C. for one hour. The resulting viscous solutions forms films which, following cure at 280° C., are wet etchable at rates comparable to those of Kapton ® (5-6 cycles) as described in Example 1.

EXAMPLE 18

Preparation of BTDA (9) //HO-BABEE (8)/R-DEDA (2)-BMI

In a one-liter flask, fitted with mechanical stirrer, thermometer, nitrogen inlet and outlet connected to a bubbler were charged 34.9 g (0.08 mole) HQ-BABEE, 7.0 g (0.02 mole) R-DEDA and 285. To the stirred solution was added in one portion 29 g (0.09 mole) BTDA causing temperature to rise to about 35° C. After stirring at room temperature for 4 hours, 4.5 g (0.046 mole) maleic anhydride was added and the mixture was stirred at room temperature for another 4 hours. The oligoamic acid was imidized by adding in quick succession 50 ml acetic anhydride, 22 ml triethylamine and 2 g anhydrous sodium acetate and stirring for 5 hours at room temperature. The oligomer was isolated by pouring the reaction mixture into stirred water and collecting by suction filtration. After several rinses with water and one with methanol the oligomer was vacuum dried overnight at 119° C.

The above flake melt flows at 170°-200° C.; Laminates made as in Example 9 give peel strengths greater than 5 pli. Cured films etch at rates comparable to Kapton ® (5-6 cycles) as described in Example 1.

EXAMPLE 19

(a) QUATREX with Resorcinol 1.3-bis(3-aminobenzoate)

Four grams (0.01 mole) Quatrex was mixed with 3.5 g (0.01 mole) R-DEDA and 20 g toluene and the mixture was heated with stirring until a homogeneous solution was obtained. Two grams of that solution was placed in a shallow aluminum weighing dish, 2.5" in diameter, and placed in an oven at 60° C. for 68 hours. During this period the resin lost all tackiness and became quite tough. Further evidence that the resin had been cured was provided by the fact that it remained tough while kept and tested for tackiness at 120° C.

(b) QUATREX with 2,2-Bis (4-aminophenoxyphenyl)propane (CONTROL)

For this CONTROL experiment, 4 g (0.01 mole) of Quatrex was mixed with 4.9 g (0.01 mole) of 2,2-Bis (4-aminophenoxyphenyl) propane and 20 g toluene. The solution was treated in the same manner as in (a) above and dried similarly to produce a tough, cured resin.

When tested with the method described in Example 1, sample (a) disintegrates in about 6-7 cycles, while sample (b) remains completely unchanged.

EXAMPLE 20

(a) Bismaleimide of Methylene Dianiline with Resorcinol 1,3-Bis (3-aminobenzoate)

A mixture of 35.8 g (0.1 mole) MDA-BMI, 34.8 g (0.1 mole) R-DEDA and 70.6 g NMP (to make 50% solids) was heated to 100° C. for 2 hours to pre-polymerize the BMI and diamine (Michael Addition). The mixture remained in solution for several days, indicating that chain extension had taken place, as compared to heating the mixture briefly to dissolve all solids, which separate immediately upon cooling. Kapton ®/copper laminates made at 170° C. and 200 psig, after removal of NMP at 160° C., followed by 1 hour cure at 260° C., had a peel strength in excess of 8 pli.

Films of the cured resin (made in shallow aluminum dishes as described in the Example 19), ca 2 mil thick, disintegrates completely after 6-7 cycles in the test described in Example 1.

(b) Bismaleimide of Methylene dianiline with Methylene Dianiline (CONTROL)

A CONTROL film of MDA-BMI and methylene dianiline made in the same manner as above, remained unaffected in the test described in Example 1.

EXAMPLE 21

Preparation of Bismaleimide of Resorcinol-1,3-Bis(3-aminobenzoate) (R-DEDA-BMI)

In a 1-liter flask fitted with mechanical stirrer, thermometer, nitrogen inlet and condenser connected to a bubbler were charged 28 g (0.29 mole) maleic anhydride and 200 ml dry acetone (reagent grade). To the stirred solution was added a solution of 44 g (0.13 mole) R-DEDA in 150 ml acetone resulting slowly in separation of yellow solids (bismaleamic acid). After stirring for one hour, 9 g triethylamine was added and the mixture was stirred for 30 minutes. To imidize, 52 ml of acetic anhydride and 1 g of magnesium chloride hexahydrate were added and the mixture was stirred at 50° C. for 3 hours, resulting in an amber solution. The reaction mixture was poured slowly in stirred, cold water/methanol (1/1 volume ratio) resulting in precipitation of cream-colored solids. The latter was collected by suction filtration, rinsed several times with water and vacuum dried at 110° C. overnight. The yield of R-DEDA-BMI, m.p. 173°-177° C., was 64.5 g (97.5%).

EXAMPLE 22

Bismaleimide of Resorcinol-1,3-Bis(3-aminobenzoate) with 1,3-Bis (4-aminophenoxy)benzene A Michael Addition formulation was prepared by heating 46.5 g (0.09 mole) of bismaleimide of resorcinol-1,3-bis(3-aminobenzoate), 26.3 g (0.09 mole) 1,3-bis(4-aminophenoxy)benzene and 89 g NMP to 112° C. for one hour. Laminates from the above mixture, made as described in Example 20, had very good adhesion (qualitative examination).

Films prepared in shallow aluminum dishes and cured at 260° C. for one hour, disintegrate as readily as the films of Example 20, according to the method described in Example 1.

What is claimed is:

1. A laminate comprising in order a metallic layer, an adhesive composition layer and an etchable polyimide layer, wherein the adhesive composition comprises a cross-linked reactive oligomer having in a backbone hydrolyzable phenolic ester groups of an equivalent weight in a range from 200 to 10,000, with the requirement that a 50 micrometer thick film of the composition after cure disintegrates within 50 cycles of alternatingly submersing the film in a stirred solution containing by weight 13% potassium hydroxide, 11% distilled water, and 76% ethanol at 60° C. for 1 minute, and in a stirred bath of deionized water at 60° C. for 30 seconds, one submersion in the ethanolic potassium hydroxide solution followed by one submersion in the deionized water, constituting one cycle.

2. A laminate as defined in claim 1, wherein the metallic film is copper.

3. A laminate as defined in claim 1, wherein the cross-linked reactive oligomer is a cross-linked epoxy.

4. A laminate as defined in claim 1, wherein the cross-linked reactive oligomer is a cross-linked oligoimide.

5. A laminate as defined in claim 1, wherein the cross-linked oligoimide has the formula:

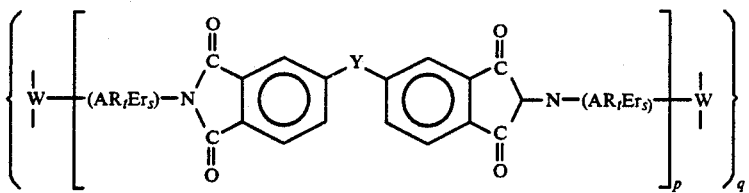

in which

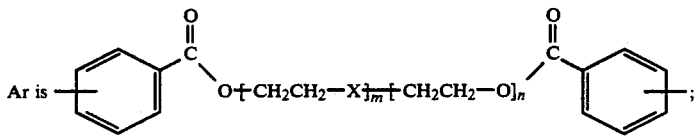

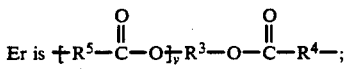

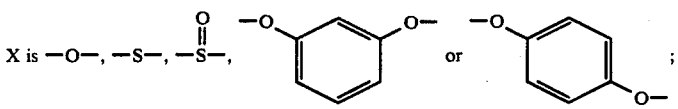

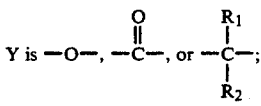

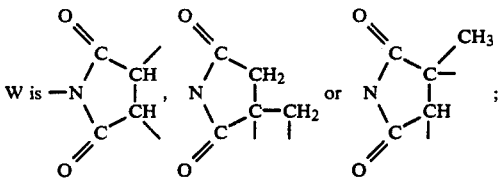

$R_1$ is —H, —CH$_3$, —C$_2$H$_5$ or —CF$_3$;
$R_2$ is —H, —CH$_3$, —C$_2$H$_5$ or —CF$_3$;
$R_3$ is a divalent radical having at least an aromatic portion through which it provides at least one of its two valencies;
$R_3$, $R_4$ and $R_5$ have molecular weights so that their sum is less than 2,000;
n is 0 to 1;
m is 0 to 1, so that m+n=1;
p is 0 to 15;
v is 0 to 1;
t is 0.95 to 0;
s is 0.05 to 1, so that t+s=1; and
q is greater than 10.

* * * * *